(12) United States Patent
Iranitalab

(10) Patent No.: US 8,366,654 B2
(45) Date of Patent: Feb. 5, 2013

(54) APPARATUS FOR PREVENTING CROSS CONTAMINATION BY STERILIZING AN INSUFFLATION DEVICE

(75) Inventor: Pajhand Iranitalab, Pleasanton, CA (US)

(73) Assignee: Stryker Corporation, Kalamazoo, MI (US)

( * ) Notice: Subject to any disclaimer, the term of this patent is extended or adjusted under 35 U.S.C. 154(b) by 315 days.

(21) Appl. No.: 12/806,300

(22) Filed: Aug. 10, 2010

(65) Prior Publication Data

US 2011/0060272 A1 Mar. 10, 2011

Related U.S. Application Data

(60) Provisional application No. 61/276,209, filed on Sep. 9, 2009.

(51) Int. Cl.
*A61M 37/00* (2006.01)
(52) U.S. Cl. .................................................... 604/26
(58) Field of Classification Search .................. 604/26; 422/24
See application file for complete search history.

(56) References Cited

U.S. PATENT DOCUMENTS

| | | | |
|---|---|---|---|
| 3,885,590 A * | 5/1975 | Ford et al. | 137/613 |
| 5,614,151 A | 3/1997 | LeVay et al. | |
| 6,299,592 B1 | 10/2001 | Zander | |
| 6,605,260 B1 * | 8/2003 | Busted | 422/186.3 |
| 6,811,748 B2 | 11/2004 | Ettlinger et al. | |
| 7,005,111 B2 | 2/2006 | Bollini | |
| 7,323,065 B2 | 1/2008 | Fencl et al. | |
| 7,326,387 B2 | 2/2008 | Arts et al. | |
| 2002/0128603 A1 * | 9/2002 | Booth et al. | 604/164.01 |
| 2005/0079096 A1 | 4/2005 | Brown-Skrobot et al. | |
| 2006/0147339 A1 | 7/2006 | Hunter et al. | |
| 2007/0187626 A1 | 8/2007 | Gaska et al. | |

* cited by examiner

*Primary Examiner* — Nicholas Lucchesi
*Assistant Examiner* — Melissa A Snyder
(74) *Attorney, Agent, or Firm* — Flynn, Thiel, Boutell & Tanis, P.C.

(57) ABSTRACT

An insufflation device connects to a disposable tube set for providing gas to fill an abdominal cavity of a patient to enable surgical procedures. The insufflation device has an ultraviolet light source to provide ultraviolet light for sterilizing a flow control valve system therein. A filter provided with the insufflation device enables additional surgical procedures for the insufflation device without cleaning of the flow control valve systems or necessarily replacement of the filter. Tube sets connected to the insufflation device do not necessarily require a filter.

21 Claims, 3 Drawing Sheets

APPARATUS FOR PREVENTING CROSS CONTAMINATION BY STERILIZING AN INSUFFLATION DEVICE

CROSS REFERENCE TO RELATED APPLICATION

This application claims the benefit of U.S. Provisional Application No. 61/276,209, filed Sep. 9, 2009, the disclosure of which is hereby incorporated by reference in its entirety.

FIELD OF THE INVENTION

This invention is directed to an arrangement for sterilizing the flow path in an insufflation device.

BACKGROUND OF THE INVENTION

Surgeons have used laparoscopic surgery to perform a variety of procedures. Such surgery, as compared to conventional surgery, reduces patient trauma, decreases patient recovery time and reduces the amount of post-operative care required.

To perform a laparoscopic procedure, a sufficient volume for the introduction of a laparoscope and other instruments must be provided by raising the abdominal wall from the organs enclosed in an abdominal cavity. Insufflation is typically obtained by pressurizing the abdominal cavity with a suitable gas, typically carbon dioxide. The presence of artificial gas in the peritoneal cavity is referred to as pneumoperitoneum.

FIG. 1 illustrates a prior art insufflator unit 10 including a housing 12 with a plurality of input elements 14a-14g and a display 16. The insufflator unit 10 includes a projecting flow output port 17 and a temperature connector 18.

FIG. 2 shows a prior art tube set 20 that includes an input connector 22 for connection to the flow output port 17 of the insufflator unit 10. The input connector 22 attaches to tubing 24. The tubing 24 of the tube set 20 includes a filter 26 provided thereon for filtering any backflow of gas/fluid. The distal end of the tubing 24 has a trocar 28 mounted thereto. The trocar 28 includes a needle type element 30 for insertion into the chest cavity of a patient to perform a surgical procedure.

A gas source (not shown) connects to the insufflator unit 10. The insufflator unit 10 controls the passage of gas therethrough and into the tube set 20. A small incision is made in the body of a patient, and one end of the trocar 28 is attached to a distal end of the tubing 24 and inserted into the abdominal cavity. The input connector 22 at the proximal end of the tube set 20 connects to the flow output port 17 of the insufflator unit that outputs the flow of gas.

In operation, the gas source provides a pressurized gas to the insufflator unit 10. A pressure regulator in the insufflator unit 10 regulates the pressure of the incoming gas and provides the gas to a valve system. The valve system includes a plurality of valves and other elements that provide a controlled flow of gas for output from the insufflator unit 10 to the tube set 20. The input elements 14a-14g are provided for adjustment of the flow of gas output from the insufflator unit 10.

The filter 26 is provided within the path of the tubing 24, and thus is an integral part of the tube set 20. The purpose of the filter 26 is to try to reduce the possibility of cross-contamination from different uses of the insufflator unit 10 with different patients. Besides cross-contamination, entry of body fluids into the insufflator unit 10 can result in repair costs. The entire tube set 20, including the filter 26 mounted thereon, is disposable.

The present invention is directed to preventing cross-contamination of patients by sterilizing a gas flow path within an insufflation device.

SUMMARY OF THE INVENTION

In one embodiment of the invention, the gas transporting flow piping is made from a transparent material. In this embodiment, one or more elongate ultraviolet lamps are provided adjacent various lengths of the transparent gas flow piping. UV light radiates through the transparent material, such as plastic or glass, to sterilize the interior surface of the gas flow pipe.

In another embodiment of the invention, the insufflation device is provided with an opaque gas transporting flow piping formed with a reflective material, such as a reflective coating thereon or with a reflective sheath disposed therein. An ultraviolet light source provides ultraviolet (UV) light into an input port that opens at one end into the gas transporting flow piping. The opening allows ultraviolet light to pass through the input port and into the gas transporting flow piping. A reflective coating or sheath on the inner wall of the gas flow piping allows the ultraviolet light to sterilize the interior of the piping. In some embodiments, multiple UV light sources are provided with corresponding multiple light transmitting input ports that connect to and open into the gas flow piping.

Figure 1:
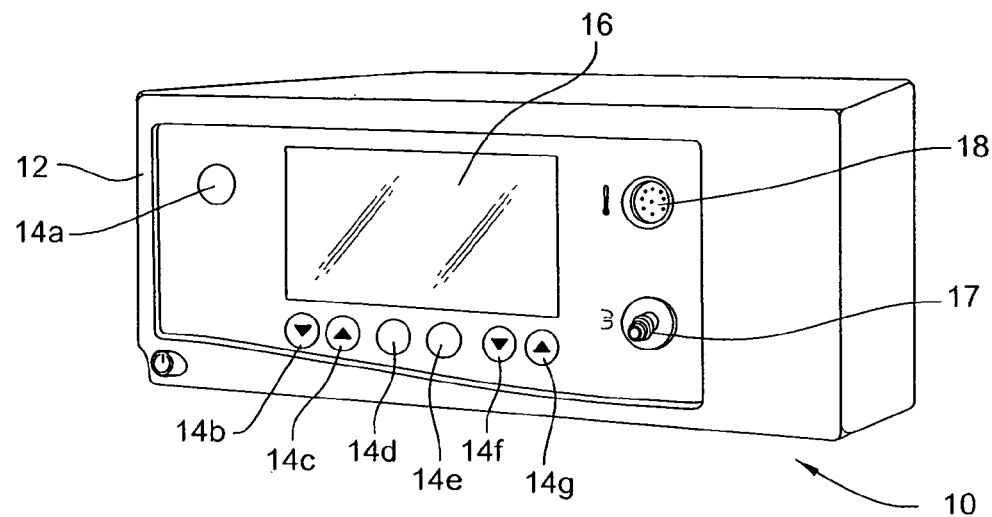
FIG. 1 depicts a perspective view of a known prior art insufflator unit.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement, and designated parts thereof. Said terminology will include the word specifically mentioned, derivatives thereof, and words of similar import.

DETAILED DESCRIPTION

Figure 3:
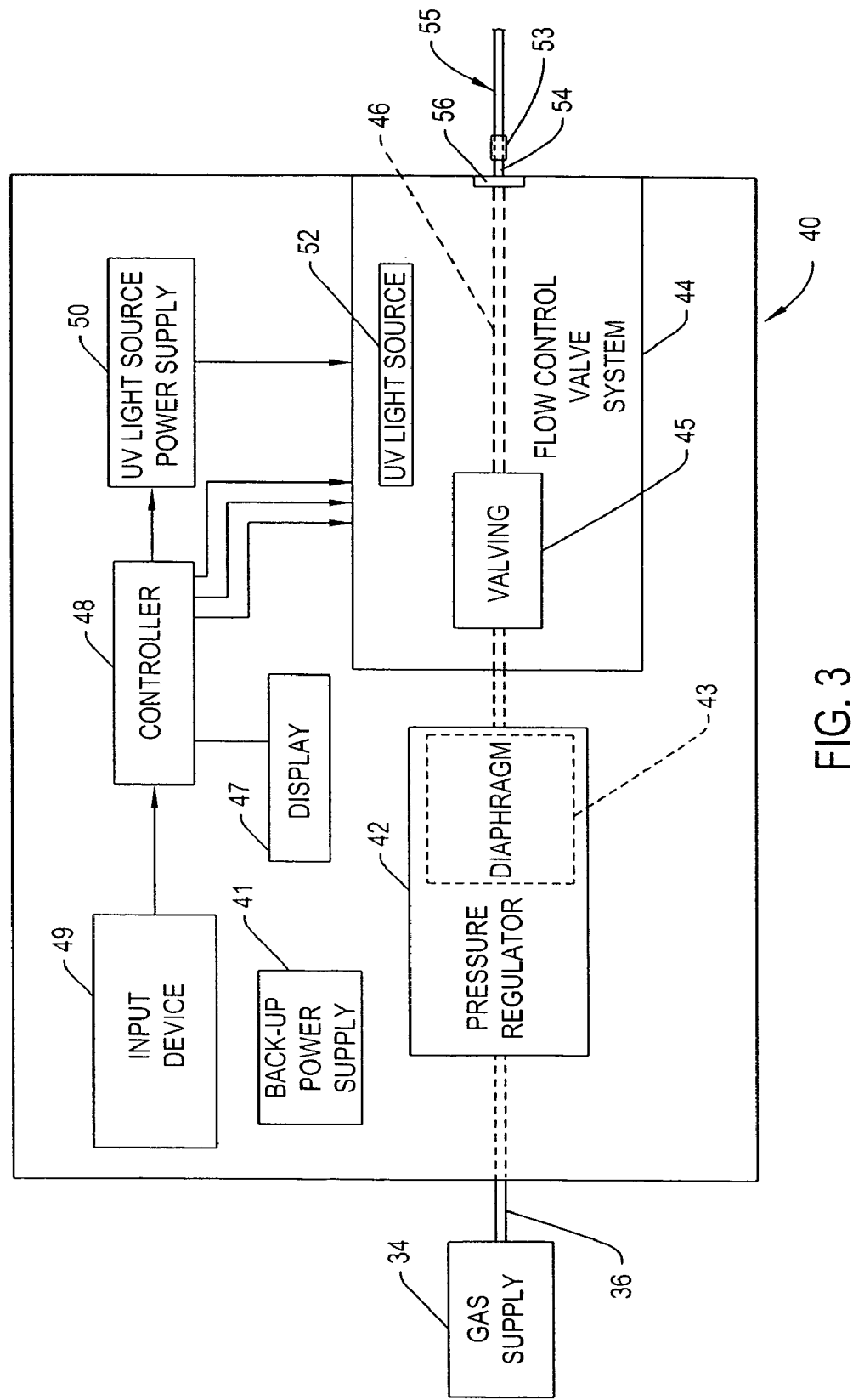
FIG. 3 is a block diagram of an insufflation device of the invention connected to a gas supply.

A gas supply 34 shown in the block diagram of FIG. 3 has an output that connects to piping 36 for carrying gas to an insufflation device 40. The insufflation device 40 includes a back-up power supply 41, such as a rechargeable battery pack, for use when the insufflation device 40 is not connected to a wall mounted power outlet. The insufflation device 40 includes a pressure regulator 42 with a diaphragm 43 that connects to a flow control valve system 44. The flow control valve system 44 includes valving 45 and output piping 46.

The valving 45 includes valve elements that are operated to control the flow of gas therethrough.

The insufflation device 40 includes an input device 49 for providing inputs to controller 48. A display 47 displays the condition of the insufflation device 40.

Controller 48 connects to the flow control valve system 44 and to a UV light source power supply 50. The UV light source power supply 50 connects to a UV light source 52 that receives power therefrom.

The flow control valve system 44 also includes a gas outlet port 54 that connects at a proximal end to the output piping 46 of the flow control valve system 44. The gas outlet port 54 projects outwardly from the insufflation device 40 for attachment to an input connector 53 of a tube set 55. Further, FIG. 3 shows a filter 56 mounted at the insufflation device 40 inwardly from the gas outlet port 54 and adjacent thereto.

Flow Control Operation

In operation, the gas supply 34 provides a high pressure gas, such as $CO_2$, to the pressure regulator 42 of the insufflation device 40. The pressure regulator 42 reduces pressure and regulates gas output at a generally constant pressure to the flow control valve system 44.

An operator utilizes the input device 49 to provide various inputs, such as desired pressure and flow rates for the gas traveling through the tube set to a patient. These inputs are communicated from the input device 49 to controller 48. In response to the inputs, the controller 48 provides one or more signals to the valving 45 of the flow control valve system 44 to control various valve elements or the like to adjust the output flow therefrom. The output gas travels through output piping 46 to the filter 56 and then through gas outlet port 54 to tube set 55.

UV Light Source Operation and Filter Function

During periods of non-use of the insufflation device 40, an operator can utilize the controller 48 to control the UV light source power supply 50 to operate the UV light source 52 for sterilizing all or part of the flow control valve system 44. Further, the UV light source 52 can operate before, during or after a medical procedure to sterilize the insufflation device 40. On cart based units, back-up power supply 41 provides power to operate the UV light source for sterilization when the insufflation device 40 is unplugged from a wall power supply outlet for transfer to a different operating room or the like.

As discussed above, FIG. 3 shows filter 56 located within the insufflation device 40 and mounted directly between the gas outlet port 54 and piping or internal tubing 46 of the flow control valve system 44. This mounting location enables the filter 56 to prevent material from entering the insufflation device 40 while enabling the gas outlet port 54 to remain for simple connection to tube set 55.

In one embodiment of the invention, the filter 56 may be utilized multiple times, for example for multiple surgical procedures, wherein the insufflation device 40 provides gas through the tube set 55 and a trocar to the interior of a patient during a surgery. The trocar utilized is essentially identical to the trocar 28 shown in FIG. 2. After a predetermined number of uses, the gas outlet port 54 is removed and the filter 56 is removed to be sterilized or replaced.

Figure 2:
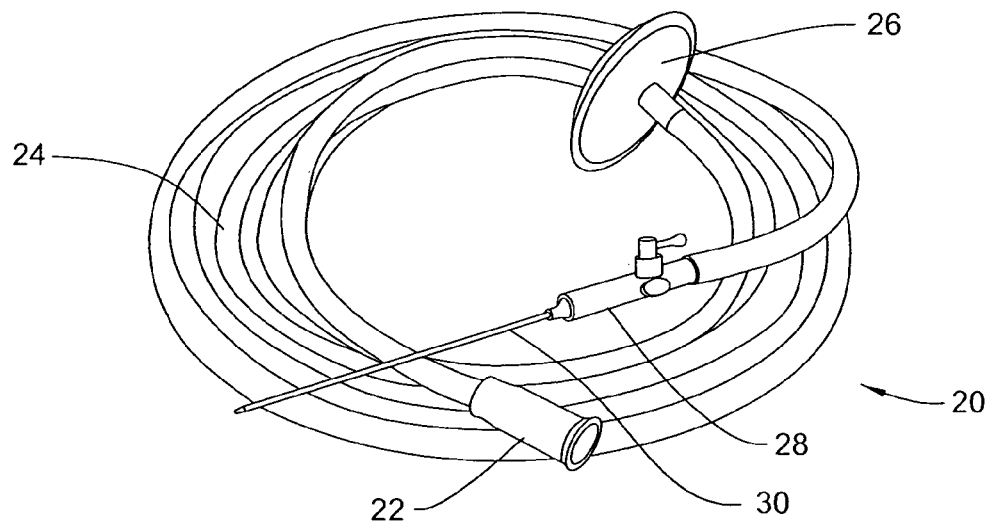
FIG. 2 depicts a known prior art tube set.

The mounting location of filter 56 enables surgical procedures to be conducted with a tube set different from that shown in FIG. 2, i.e. a tube set that is not provided with a filter, such as filter 26 shown in FIG. 2. In some embodiments, the filter 56 can be retained for multiple uses. Thus, the cost of disposable tube sets for surgical procedures can be decreased, as the filter is no longer a necessary element thereof.

Alternatives

Figure 4:
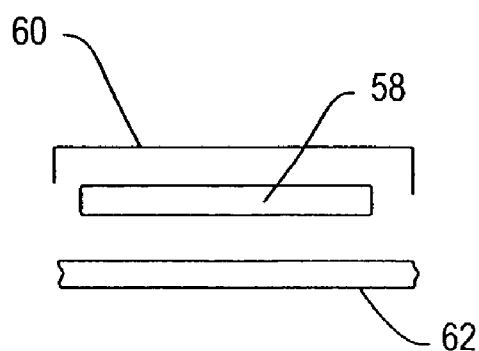
FIG. 4 shows a portion of a flow control valve system and a UV lamp.

FIG. 4 shows an alternative embodiment of the flow control valve system 44 wherein an elongate UV lamp 58 provided with a reflecting element 60, such as a mirror, emits UV radiation toward transparent piping 62 of the flow control valve system 44. The transparency of the piping 62 enables UV radiation to travel therethrough and sterilize the interior thereof. While FIG. 4 shows a single UV lamp 58, if necessary, a plurality of UV lamps 58 can be provided to sterilize the transparent piping 62, and in some instances, additional transparent piping throughout the flow control valve system 44.

Figure 5:
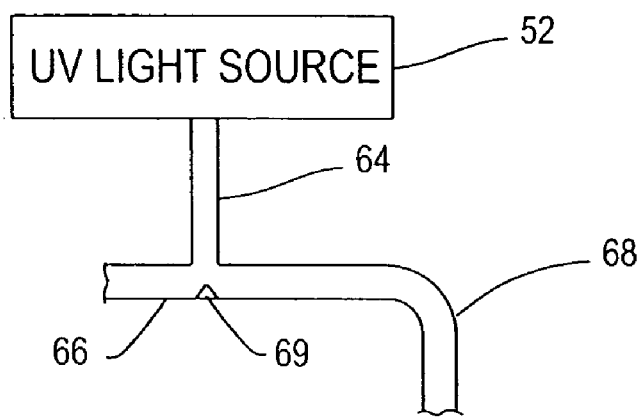
FIG. 5 shows an embodiment of a UV lamp unit that connects to a portion of a flow control valve system.

In another embodiment of the invention illustrated in FIG. 5, UV light source 52 outputs UV light into a first end of a light input port 64 that opens at a second end into an opaque piping 66 of the flow control valve system 44. In one embodiment, the opaque piping 66 is a metal piping having a polished inner surface or a reflective inner coating. The polished inner surface enables reflection of UV light within the piping 66 including about or along the piping bend 68 as shown in FIG. 5. The UV light sterilizes the interior of the piping 66, along with the interior of piping bend 68. Further, in FIG. 5, a mirror 69 formed within the inner wall of the opaque piping 66 has two faces that reflect UV light in opposing directions within the piping 66.

In another embodiment, the opaque piping 66 comprises an optic fiber that reflects UV light.

In another embodiment, the reflective material within the opaque piping 66 is replaced with a reflective sheath disposed therein or a reflective tape applied to the inner surface of the opaque piping 66.

FIG. 5 shows the light input port 64 mounted perpendicularly to the longitudinal axis of the opaque piping 66. In other embodiments, the input port 64 may be transversely oriented or angled with respect to the longitudinal axis of the piping or even enter the piping at a bend thereof, such as at a 90° bend wherein the light input port is substantially aligned or coaxial with a longitudinal axis of a section of the piping.

Figure 6:
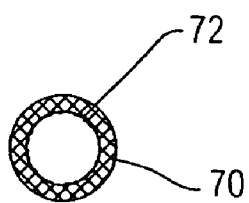
FIG. 6 illustrates a coated opaque pipe.

The embodiment of FIG. 6 shows an opaque pipe 70 having a reflective material, such as reflective coating 72, about the entirety of the inner surface thereof. The reflective coating 72 enables the transmission of UV light within and along the interior length of the opaque pipe 70. In another embodiment, the reflective material is disposed within the entirety of the body of the opaque pipe 70 and reflects UV light applied to the inner wall.

Figure 7:
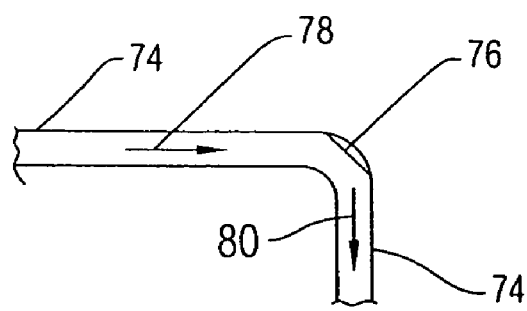
FIG. 7 depicts a pipe having an elbow with a reflective element disposed thereat.

The embodiment of FIG. 7 shows a portion of a flow control valve system 44 including an opaque piping 74 having a mirror or other reflective element 76 mounted at an elbow therein. In this embodiment, the reflective element 76 assists in transmitting UV light traveling along one path as represented by arrow 78 to another path represented by arrow 80 within the opaque piping 74.

While FIG. 3 illustrates the filter 56 mounted at or adjacent the gas outlet port 54, in other embodiments the filter 56 may be mounted to the distal end of the gas outlet port 54 and have a filter output port for connection to a tube set. More importantly, in some embodiments, filter 56 can be reusable by subjecting same to UV light radiation to sterilize filter surfaces.

In another embodiment, filter 56 is not provided in or near the insufflation device 40. Instead, a tube set filter 26 is provided with the disposable tube set in a conventional manner as shown in FIG. 2. The ultraviolet light source 52 sterilizes essentially the entirety of, or portions of, the piping of the flow control valve system 44 to reduce the possibility of cross-contamination within the insufflation device 40, as compared to a conventional insufflation device.

In some embodiments, the gas supply 34 is a gas supply provided to the insufflation device 40 by piping within a medical building. In other embodiments, the gas supply 34 is an individual type of gas canister connected to an input port of the insufflation device 40. In most embodiments, the pressure regulator 42 is a diaphragm type that avoids sudden changes in pressure.

The flow control valve system 44 is represented by a block element in FIG. 3. The flow control valve system 44, however, typically has a plurality of flow paths, such as primary and secondary flow paths, along with plural flow control valves, or the like. One example of an insufflation flow control valve system is disclosed in U.S. Pat. No. 6,299,592, the disclosure of which is hereby incorporated by reference.

In some embodiments, the flow control valve system 44 includes portions of piping that are metal, other portions of piping that are a solid transparent material, and finally other sections that are defined by a flexible transparent tubing.

In some embodiments, the input device is a touchscreen that is combined with the display 47 of the insufflation device 40. In other embodiments, the input device 46 is a foot pedal or a wireless portable remote input device.

While a UV lamp 58 is shown as the UV light source in FIG. 4, in some embodiments the UV light source 52 includes ultraviolet light emitting diodes or other UV light source arrangements.

In some embodiments, the controller 48 automatically operates the UV light source 52 for a predetermined time period after the insufflator device 40 stops providing fluid at the distal end of the output piping 46.

In other embodiments, the controller 48 powers the UV light source 52 during a surgical procedure a predetermined time after the insufflation device 40 starts operating. The UV light source 52 also can be operated at timed intervals during a surgical procedure. Finally, in some embodiments the UV light source 52 operates continuously or at different intervals and at different output power values.

Throughout the application, the term "gas" represents the input and output of the insufflation device 40. As utilized herein, gas includes $CO_2$. In some embodiments, water vapor is also provided and in some instances, the gas has a predetermined humidity value. Therefore the term "gas", as used herein, includes liquid components typically provided in a gaseous form.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. An insufflation device comprising:
    an insufflation device housing;
    an input pipe having a first end for receiving gas from a gas supply;
    a pressure regulator disposed within the housing and having a fluid input that is in fluid communication with a second end of the input pipe for receiving gas from the gas supply, said pressure regulator for regulating pressure of a gas received by the input pipe;
    a flow control valve system including valving disposed within the housing having a first input end in fluid communication with a gas output of the pressure regulator, said flow control valve system at a second output end including output piping for providing gas to a tube set;
    an input device for obtaining inputs from a user and generating input signals to operate the insufflation device;
    at least one ultraviolet light source disposed in the housing for applying ultraviolet light to at least a portion of the flow control valve system for sterilizing at least an inner wall of at least a portion of the output piping; and
    a controller disposed in the housing capable of receiving input signals from the input device relative to the pressure of the gas and relative to the ultraviolet light source, and capable of controlling the flow control valve system to provide a selected pressure of gas exiting the insufflation device and capable of operating the at least one ultraviolet light source.

2. The insufflation device according to claim 1, comprising:
    a light input port providing a path to an interior of said output piping for ultraviolet light that is output by said ultraviolet light source; and
    a reflective material about the entirety of the inner surface of said output piping along a predetermined length thereof, a portion of the output piping comprising a metal pipe whereat the reflective material is disposed about the inner surface thereof,
    wherein UV light traveling from said ultraviolet light source through said light input port and into the output piping is reflected by said reflective material to sterilize the inner wall of said output piping.

3. The insufflation device according to claim 2, wherein said input port comprises an optic fiber having an end that opens into the output piping.

4. The insufflation device according to claim 1, wherein said insufflation device is free from a filter along the output piping or adjacent the end of said output piping at a wall of the housing.

5. The insufflation device according to claim 1, further comprising a power supply for supplying power to the ultraviolet light source, the ultraviolet light source comprising an ultraviolet lamp.

6. The insufflation device according to claim 1, wherein the controller automatically operates the ultraviolet light source for a predetermined time period after the insufflation device stops providing fluid to the distal end of the output piping.

7. The insufflation device according to claim 2, wherein the reflective material comprises a reflective coating or a reflective sheath.

8. The insufflation device according to claim 1, wherein the output piping comprises flexible transparent plastic piping.

9. The insufflation device according to claim 1, including a gas outlet port disposed at the distal end of the output piping and at the outer surface of the insufflation device housing for providing a connection to a tube set.

10. The insufflation device according to claim 1, further comprising a back-up power supply for enabling operation of the ultraviolet light source of the insufflation device when the insufflation device is disconnected from a wall mounted power outlet.

11. The insufflation device according to claim 1, wherein the controller controls power to the ultraviolet light source for at least one interval a predetermined time after the insufflation device provides gas to a surgical site.

12. The insufflation device according to claim 1, comprising mirrors for directing ultraviolet light from the ultraviolet light source onto the inner wall of the output piping, the ultraviolet light source comprising an ultraviolet lamp.

13. The insufflation device according to claim 1, wherein said pressure regulator includes a diaphragm for regulating pressure.

14. The insufflation device according to claim 13, wherein the valving comprises a plurality of valve elements for adjusting the flow rate of fluid exiting from the output piping, wherein the valve elements are controlled by said controller.

15. The insufflation device according to claim 1, the ultraviolet light source comprising a plurality of ultraviolet lamps for providing ultraviolet light along essentially the entirety of the output piping for destroying bacteria and viruses disposed therein and for preventing cross contamination of surgical patients.

16. The insufflation device according to claim 15, wherein each said ultraviolet lamp is provided with a corresponding mirror for reflecting ultraviolet light toward the output piping.

17. An insufflation system comprising:
a tube set having flexible tubing and a proximal end for connection to an insufflation device and a distal end having a trocar thereat;
an insufflation device comprising:
an insufflation device housing;
an input pipe having a first end for receiving fluid from a gas container;
a pressure regulator disposed within the housing and having a fluid input that is in fluid communication with a second end of the input pipe for receiving fluid from the gas container, said pressure regulator for regulating pressure of a gas received by the input pipe;
a flow control valve system including valving disposed within the housing and having a first input end in fluid communication with a fluid output of the pressure regulator, said flow control valve system at a second output end including output piping for providing gas to the proximal end of said tube set;
an input device for obtaining inputs of a selected pressure value from a user and generating input signals to operate the insufflation device;
a controller disposed in the housing for receiving the input signals from the input device, the controller operating the flow control valve system to control pressure of the fluid such that the fluid exiting the insufflation device is at the selected pressure value; and
at least one ultraviolet light source disposed in the housing for applying ultraviolet light to at least a portion of the flow control valve system for sterilizing an inner wall of at least a portion of the output piping, wherein said insufflation system is capable of pressurizing the abdominal cavity of a patient.

18. The insufflation system of claim 17, wherein said tube set is free from a filter.

19. The insufflation device according to claim 17, wherein the controller is capable of controlling operation of the at least one ultraviolet light source.

20. An insufflation device comprising:
an insufflation device housing;
an input pipe having a first end for receiving gas from a gas supply;
a pressure regulator disposed within the housing and having a fluid input that is in fluid communication with a second end of the input pipe for receiving gas from the gas supply, said pressure regulator for regulating pressure of a gas received by the input pipe;
a flow control valve system including valving disposed within the housing having a first input end in fluid communication with a gas output of the pressure regulator, said flow control valve system at a second output end including output piping for providing gas to a tube set, said output piping comprising a transparent or translucent pipe for enabling the passing of ultraviolet light through the transparent or translucent pipe and into the interior of said output piping to sterilize an inner wall of at least a portion of the output piping;
an input device for obtaining inputs from a user and generating input signals to operate the insufflation device;
a controller disposed in the housing for receiving the input signals from the input device, and for controlling the flow control valve system to provide a selected pressure value for gas exiting the insufflation device; and
at least one ultraviolet light source disposed in the housing for applying ultraviolet light to at least a portion of the flow control valve system for sterilizing at least an inner wall of at least a portion of the output piping.

21. An insufflation device comprising:
an insufflation device housing;
an input pipe having a first end for receiving gas from a gas supply;
a pressure regulator disposed within the housing and having a fluid input that is in fluid communication with a second end of the input pipe for receiving gas from the gas supply, said pressure regulator for regulating pressure of a gas received by the input pipe;
a flow control valve system including valving disposed within the housing having a first input end in fluid communication with a gas output of the pressure regulator, said flow control valve system at a second output end including output piping for providing gas to a tube set, the output piping having a distal end;
an input device for obtaining inputs from a user and generating input signals to operate the insufflation device;
a controller disposed in the housing for receiving the input signals from the input device, and for controlling the flow control valve system to provide a selected pressure value for gas exiting the insufflation device;
at least one ultraviolet light source disposed in the housing for applying ultraviolet light to at least a portion of the flow control valve system for sterilizing at least an inner wall of at least a portion of the output piping;
a gas outlet port disposed at the distal end of the output piping and at the outer surface of the insufflation device housing for providing a connection to a tube set; and
a removable filter mounted between the distal end of the output piping and a proximal end of the gas outlet port, wherein the filter is removable from the insufflation device for cleaning or replacement, and wherein the tube set for use with the insufflation device is free from a filter.

* * * * *